United States Patent [19]

Masuda

[11] Patent Number: 4,894,670
[45] Date of Patent: Jan. 16, 1990

[54] SLIT PROJECTION APPARATUS

[75] Inventor: Takashi Masuda, Kawasaki, Japan

[73] Assignee: Canon Kabushiki Kaisha, Tokyo, Japan

[21] Appl. No.: 145,408

[22] Filed: Jan. 19, 1988

[30] Foreign Application Priority Data

Jan. 26, 1987 [JP] Japan ................................. 62-15753

[51] Int. Cl.$^4$ .............................................. A61B 3/10
[52] U.S. Cl. ..................................... 351/214; 351/205
[58] Field of Search ........................ 351/205, 214, 221

[56] References Cited

U.S. PATENT DOCUMENTS

| | | | |
|---|---|---|---|
| 3,433,560 | 3/1969 | Gambs | 351/214 |
| 3,535,027 | 10/1970 | Littmann et al. | 351/214 |
| 3,944,343 | 3/1976 | Mueller | 351/214 |

Primary Examiner—Rodney B. Bovernick
Attorney, Agent, or Firm—Fitzpatrick, Cella, Harper & Scinto

[57] ABSTRACT

A slit projection apparatus has slit light beam forming means and a projection optical system for projecting a slit image onto an object to be examined. The projection optical system is provided with a light deflecting member rotatable so as to form a predetermined elevation angle, and a lens system having a predetermined focal length corresponding to the angle of rotation of the light deflecting member so as to compensate for the optical path difference conforming to said angle of rotation and including a lens having at least a portion thereof movable in the direction of the optic axis while keeping a predetermined spacing with respect to the light deflecting member.

13 Claims, 3 Drawing Sheets

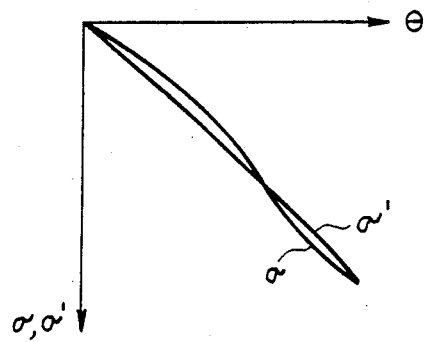
F I G. 6

SLIT PROJECTION APPARATUS

BACKGROUND OF THE INVENTION

This invention relates to a slit projection apparatus having a mechanism for tilting a projected slit image.

RELATED BACKGROUND ART

The slit lamp examination in which a slit image is projected onto an eyeball and the light-sectioned image thereof is enlarged and observed by the use of a slit lamp utilizing the fact that the eyeball is not a completely transparent body and the light incident thereon is scattered though slightly is widely practised in ophthalmic examination and treatment. Also, observation of the fundus and front cell corner of an eye is practiced with a contact lens mounted on the eye.

If at this time, the regularly reflected light from the cornea or the crystalline lens or the surface of the contact lens is eliminated, the observation is hindered, and this sometimes leads to the necessity of projecting the slit image from an oblique direction relative to the direction of observation. Now, in the conventional slit lamp, a projection optical system and an observation microscope are rotatable in a horizontal plane about the imaging point, and when the slit image faces in a vertical direction, the optical path can be simply inclined. However, when the slit image faces in a horizontal direction, the apparatus must be vertically inclined, and this is realized by the use of a complicated mechanism or an image rotator as an improvement thereof.

Now, in Japanese Laid-Open Patent Application No. 14829/1987, there is disclosed a tilting mechanism utilizing a bypass optical path using a mirror with a lens being fixed, and a conventional typical tilting mechanism in which a lens system is moved in the direction of the optic axis is shown in FIG. 7 of the accompanying drawings. In FIG. 7, a light emitted from a light source 1 passes through a condenser lens 2, a slit 3 and a filter 4, is collimated by a collimator lens 5, further passes through an image rotator 6 and is refracted by a projection lens 7, and the light source image L is formed near a prism 8, and further the optical path is bent by a prism 8, whereby a slit image S is formed. In this projection optical system, to direct the slit image in a horizontal direction and change the direction of projection thereof by $\theta$, the image rotator 6 is rotated and the change in the optical path resulting from movement is compensated for as indicated by arrow and dotted lines and therefore, the projection lens 7 and the prism 8 must be independently moved by a predetermined distance in the direction of the optic axis and at the same time, the prism 8 must be inclined by $\theta/2$ with respect to the optic axis.

SUMMARY OF THE INVENTION

The object of the present invention is to provide a slit projection apparatus which can accomplish the movement of a light deflecting member and a lens in the direction of the optic axis by a simple mechanism when a predetermined elevation angle is to be formed.

BRIEF DESCRIPTION OF THE DRAWINGS

FIGS. 1 to 6 show an embodiment of a slit projection apparatus according to the present invention, FIG. 1 showing the construction of the present invention, FIGS. 2(a) and (b) and FIGS. 3(a) and (b) being illustrations of the optical system, FIG. 4 showing the relation between the elevation angle $\theta$ and the amount of variation $\sigma'$ in the length of the optical path and the amount of variation $\sigma$ in the lens back, FIGS. 5(a) and (b) being illustrations of a projection optical system as another embodiment, and FIG. 6 showing the relation between the elevation angle $\theta$ and the amount of variation $\sigma'$ in the length of the optical path and the amount of variation $\sigma$ in the lens back in the optical system as said another embodiment.

DESCRIPTION OF THE PREFERRED EMBODIMENTS

Figure 1:
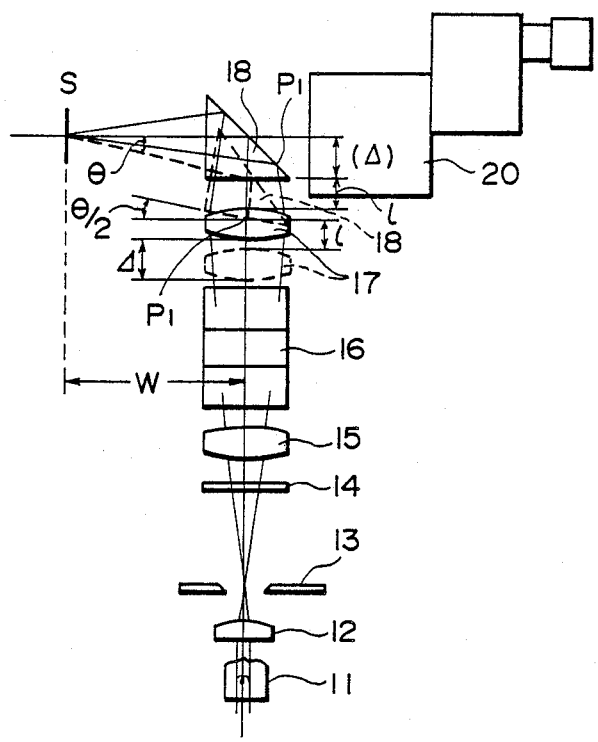

Referring to FIG. 1 which shows the construction of an embodiment of the present invention, the reference numeral 11 designates a light source such as a halogen incandescent lamp. On the optic axis of the light source 11, there are disposed in succession a condenser lens 12, a slit 13, an interchangeable filter 14, a projection lens 15, an image rotator 16 for rotating the optical path, a projection lens 17 movable along the optic axis, and a prism 18 rotatable about any axis P1 perpendicular to the plane of the drawing sheet and movable along the optic axis. Also, on the extension of a line passing through the projection position (a slit image S) and the prism 18 (the solid-line position), there is disposed a stereoscopic microscope 20 for enlarging and observing the projected image therethrough. A stage unit for moving the entire apparatus back and forth, horizontally and vertically to effect position adjustment relative to an eye to be examined, and a mechanism for rotating the projection optical system and the stereoscopic microscope 20 in a horizontal plane about the slit image S projected onto the eye to be examined are not shown in FIG. 1.

A light beam emitted from the light source 11 illuminates the slit 13 by the condenser lens 12, passes through the filter 14, the projection lens 15 and the image rotator 16, enters the projection lens 17 as a non-parallel light beam and passes through the projection lens 17, has its direction changed by the prism 18 and forms the slit image S at the projection position and thus, this image is observed through the stereoscopic microscope 20. Also, when projection is to be effected as a slit image S whose lengthwise direction faces in the horizontal direction with an elevation angle $\theta$, the image rotator 16 is rotated and the projection lens 17 and the prism 18 are lowered by a distance $\Delta$ in the direction of the optic axis while the distance l between the projection lens 17 and the prism 18 is kept constant as indicated by dotted line in FIG. 1, and further, the prism 18 is rotated by $\theta/2$ about any center of rotation P1.

Figure 2:
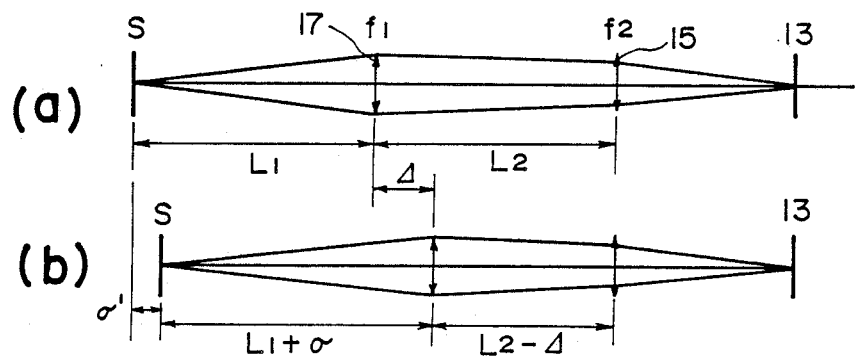

FIGS. 2(a) and (b) represent the positional relations between the projection lenses 15, 17 and the slit 13 and the slit image S, FIG. 2(a) showing a state in which the slit image S is projected from a substantially horizontal direction, and FIG. 2(b) showing a state in which the slit image S is projected with an elevation angle $\theta$. In FIG. 2(a), the focal lengths of the projection lenses 15 and 17 are f1 and f2, respectively, the optical equivalent distance from the slit image S to the projection lens 17 is L1, and the optical distance between the projection lenses 15 and 17 is L2. In FIG. 2(b), the projection lens 17 has been moved by $\Delta$ in the direction of the optic axis, and this figure shows that along therewith, the distance from the projection lens 17 to the slit image S, i.e., the so-called lens back of the projection lens 17, changes by $\sigma$ from L1 to L1+$\sigma$.

Figure 3:
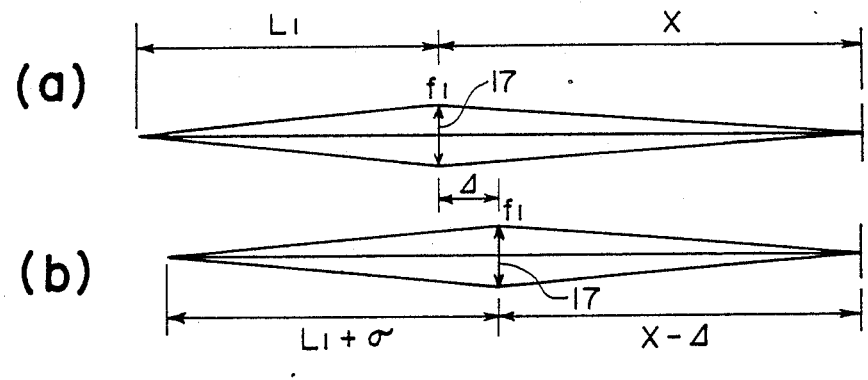

FIGS. 3(a) and (b) show the imaging relations of the projection lens 17 in FIGS. 2(a) and (b), and in these figures, the distance from the projection lens 17 to the image of the slit 13 by the projection lens 17 is x, and the focal length of the projection lens 17 is f1. Thus, from FIG. 3(a), geometrooptically, the relation that $$1/x + 1/L1 = 1/f1 \tag{1}$$

is established, and from FIG. 3(b), the relation that $$1/(x - \Delta) + 1/(L1 + \sigma) = 1/f1 \tag{2}$$

is established. If x is eliminated from equations (1) and (2), the relation that $$f1^2 \cdot (\Delta - \sigma) = \Delta \cdot L1 \cdot (f1 - L1 - \sigma) \tag{3}$$

is derived.

On the other hand, from FIGS. 2(a) and (b), $L1 + \Delta = \sigma' + (L1 + \sigma)$, that is, $$\Delta = \sigma + \sigma' \tag{4}$$

Also, approximately, the following equation is established:

$$\sigma' = \left(\Delta + \frac{\Delta}{\tan \theta}\right) - \frac{\Delta}{\sin \theta} = \Delta \tan \frac{\theta}{2} \tag{5}$$

From equations (4) and (5), $$\sigma = \Delta \left(1 - \tan \frac{\theta}{2}\right) \tag{6}$$

Further, when in FIG. 1, the spacing between the slit image S and the optic axis of the lenses 15, 17 is W, the following equation is approximately established:

$$\Delta = W \tan \sigma \tag{7}$$

From equations (3), (6) and (7), $$A \cdot f1^2 + B \cdot f1 + C = 0 \tag{8}$$

where $A = \tan \theta/2$, $B = -L1$, and $C = L1^2 + WL1\tan \theta(1 - \tan \theta/2)$.

That is, the focal length f1 is determined from equation (8) so that the lens back reflected from the projection lens 17 by the prism 18 and leading to the slit image S when the slit image S is projected from the substantially horizontal direction depicted by solid line in FIG. 1 is L1 and the lens back when the projection lens 17 and the prism 18 are both moved by the distance $\Delta$ to the state depicted by broken line and the slit image S is projected with the elevation angle $\theta$ is (L1+$\sigma$).

In the calculation of equations (5) and (6), a similar result will be obtained even if the prism 18 is replaced by a mirror having the same reflecting surface as that of the prism.

The focal length f2 of the projection lens 15 is suitably selected in accordance with the length of the optical path between the projection lenses 15 and 17 including the image rotator 16 and the magnifications of the slit 13 and the slit image S.

Now, when the elevation angle $\theta$ is to be continuously varied, it is possible to adopt a structure in which the angle of rotation $\theta/2$ of the prism 18 and the amount of movement $\Delta$ of the projection lens 17 and the prism 18 are continuously varied in association with each other as by a cam mechanism.

Figure 4:
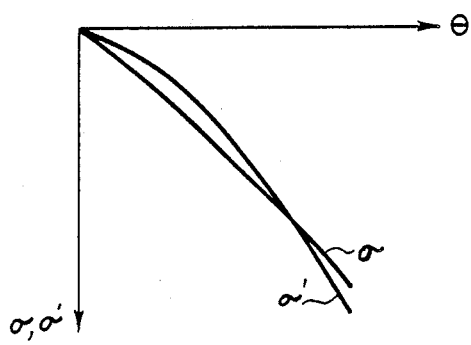

In such case, however, if the focal length of the projection lens 17 is fixed, the relation that $\sigma + \sigma' = \Delta$ is not always established between the amount of variation $\sigma'$ in the length of the optical path measured from the projection lens 17 along the optic axis with the elevation angle $\theta$ as a parameter and the amount of variation $\sigma$ in the lens back of the lens 17 (the distance between the lens and the image), as shown in FIG. 4, and the defocus of the slit image S occurs. However, by suitably selecting each parameter of the optical system, it is possible to establish the relation that $\sigma + \sigma' = \Delta$ as far as possible.

Incidentally, if the slit image S is projected by a lens system comprising a convex lens $L_1$, concave lens $L_2$ and a convex lens $L_3$ as shown in FIGS. 5(a) and (b), the amount of variation $\sigma'$ in the length of the optical path and the amount of variation $\sigma$ in the lens back can be corrected at three points as shown in FIG. 6 by moving the convex lenses $L_1$ and $L_3$ by an equal distance in the same direction at a time while the concave lens $L_2$ remains fixed, whereby the aforementioned defocus amount can be reduced.

If the projection lens 17 (for example, a zoom lens is employed as the projection lens 17) is designed such that the focal length f1 thereof varies in conformity with the elevation angle $\theta$ so that equation (8) is always satisfied, the slit image will ideally always be focused irrespective of the elevation angle $\theta$.

Now, according to the present invention, the prism 18 and the lens 17 may be moved by an equal amount in the direction of the optic axis and therefore, the prism 18 and the lens 17 can be moved together in the direction of the optic axis and thus, use can be made of any moving mechanism of a well-known simple structure (for example, a screw feed mechanism). The $\theta/2$ rotation of the prism 18 may take place with the movement of the prism 18 in the direction of the optic axis, or before or after the movement of the prism 18 in the direction of the optic axis.

Figure 5:
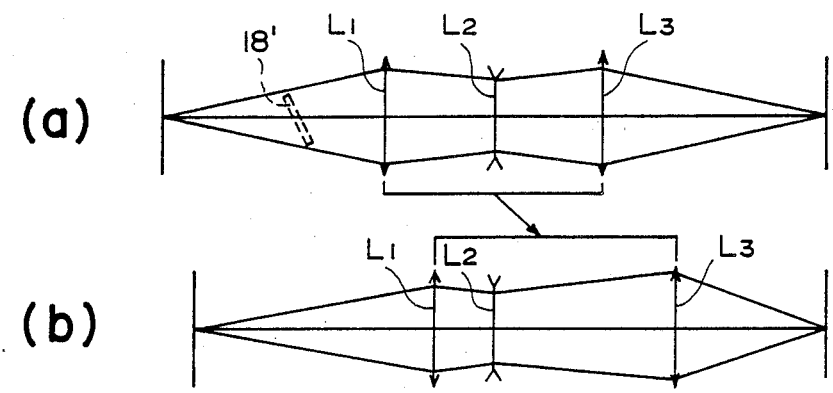
Figure 7:
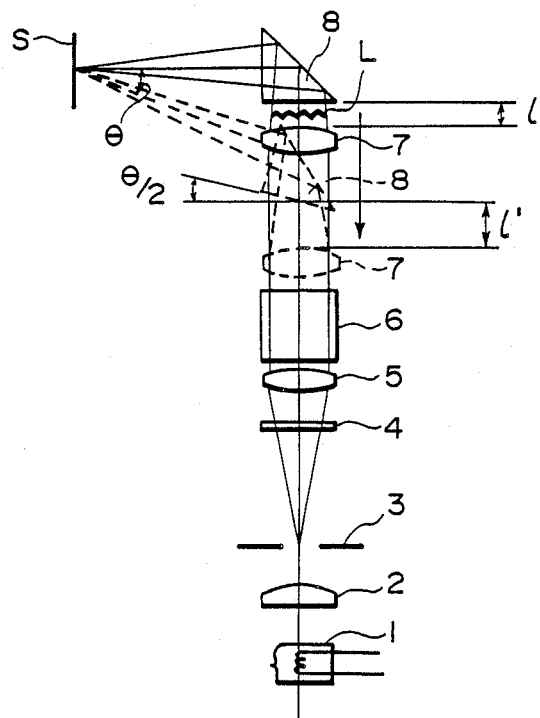
FIG. 7 shows the construction of an example of the prior art.

The present invention is not restricted to the above-described embodiment, but as indicated by broken line in FIG. 5, the prism 18 may be realized by a reflecting mirror 18' such as a plane mirror. The image rotator 16 will become unnecessary if the slit 13 itself is rotatable about the optic axis.

I claim:

1. A slit projection apparatus comprising:
   slit light beam forming means;
   a projection optical system for projecting a slit image onto an object to be examined in at least first and second elevation angles, said projection optical system including means for maintaining the slit and the object conjugate to each other when projecting the slit image in the first and second elevation angles, said projection optical system being provided with a light deflecting member which is movable in the direction of the optical axis of said projection optical system and is rotatable for generating the at least first and second elevation angles and at least a lens which is movable with said light deflecting member in the direction of the optical axis of said projection optical system in accordance with changes in the elevation angle; and means for moving said light deflecting member and said lens in a body in the direction of the optical axis.

2. A slit projection apparatus according to claim 1, wherein said light deflecting member is a prism.

3. A slit projection apparatus according to claim 1, wherein said light deflecting member is a mirror.

4. A slit projection apparatus according to claim 1, wherein said projection optical system is provided with an image rotator capable of rotating the slit image about the optic axis.

5. A slit projection apparatus according to claim 1, wherein the object to be examined is an eye to be examined.

6. A slit projection apparatus according to claim 1, wherein the total focal length of said projection optical system is equal to the focal length of said lens and is fixed during the first elevation angle and the second elevation angle.

7. A slit projection apparatus according to claim 1, wherein said projection optical system further comprises a second lens, the total focal length of said projection optical system varying when changing from the first elevation angle to the second elevation angle.

8. A slit projection apparatus according to claim 1, wherein the slit is projected onto the object from a substantially horizontal direction in the first elevation angle.

9. A slit projection apparatus comprising:
slit light beam forming means;
a projection optical system for projecting a slit image onto an object to be examined in at least first and second elevation angles, said projection optical system including means for maintaining the slit and the object conjugate to each other when projecting the slit image in the first and second elevation angles, said projection optical system being provided with a light deflecting member which is movable in the direction of the optical axis of said projection optical system and is rotatable, for generating the at least first and second elevation angles and at least a lens system which is movable with said light deflecting member in the direction of the optical axis of said projection optical system in accordance with changes in the elevation angle; and
means for moving said light deflecting member and said lens system in a body in the direction of the optical axis, wherein said projection optical system is provided with a convex lens, a concave lens, and a convex lens adjacent the object, said convex lens, said concave lens and said convex lens adjacent the object being arranged in the order named, said two convex lens as said lens system being movable and said concave lens being fixed when the elevation angle is changed from the first elevation angle to the second elevation angle.

10. A slit projection apparatus according to claim 7, wherein said second lens is a fixed lens.

11. A slit projection apparatus according to claim 9, wherein one of said first elevation angle and said second elevation angle is zero degrees.

12. A slit projection apparatus according to claim 9, wherein both said first and second elevation angles are greater then zero degrees.

13. A slit projection apparatus for projecting a slit image to an eye to be examined from a horizontal direction or a predetermined elevation angle, comprising:
a light reflection member located at a position apart from the eye to be examined by a predetermined distance, $W$;
an imaging lens system having a lens which is located on an optical axis of a light flux reflected by said light reflection member at a position apart form the eye to be examined by a distance, $L_1$, in the direction of the optical axis when said light reflection member is at a position in the horizontal direction with respect to the eye to be examined;
a light flux generation means for projecting an image of a slit to the eye to be examined through said imaging lens system and from said light refection member; and
means for moving said light reflection member and said lens in a body in the direction of the optical axis, wherein said light reflection member is rotatable to change a projection angle, $\Theta$ of the slit image to the eye to be examined and is movable on the optical path of a light projected from a side of the eye to be examined and reflected by said light reflection member by a predetermined amount, $\Delta$, and wherein said lens has a focal length, $f_1$, substantially satisfying an equation:

$$Af_1^2 + Bf_1 + C = 0$$

and wherein said lens is movable on an optical axis of a light projected form a side of the eye to be examined and reflected by said light reflection member in the same direction and by the same amount, $\Delta$, as said light reflection member, where, $A = \tan\Theta/2$, $B = -L_1$, and $C = L_1^2 + WL_1\tan\Theta(1 - \tan\Theta/2)$.

* * * * *

UNITED STATES PATENT AND TRADEMARK OFFICE
CERTIFICATE OF CORRECTION

PATENT NO. : 4,894,670

DATED : January 16, 1990

INVENTOR(S) : Takashi Masuda

It is certified that error appears in the above-identified patent and that said Letters Patent is hereby corrected as shown below:

COLUMN 6:

Line 3, "convex lens" should read --convex lenses--.

Line 23, "form" should read --from--.

Line 31, "light refection" should read --light reflection--.

Line 47, "form" should read --from--.

Signed and Sealed this

Twenty-sixth Day of May, 1992

Attest:

DOUGLAS B. COMER

Attesting Officer

Acting Commissioner of Patents and Trademarks